(12) United States Patent
Sakurai et al.

(10) Patent No.: US 6,458,828 B1
(45) Date of Patent: Oct. 1, 2002

(54) DEODORANTS, FOODS AND BEVERAGES, AND ORAL COMPOSITIONS AS WELL AS TOILETRY PRODUCTS

(75) Inventors: Koji Sakurai; Hideyuki Yasuda; Masayoshi Makino; Hiroko Ogiwara; Shingo Konno, all of Saitama (JP)

(73) Assignee: Lotte Co., Ltd., Tokyo (JP)

( * ) Notice: Subject to any disclaimer, the term of this patent is extended or adjusted under 35 U.S.C. 154(b) by 4 days.

(21) Appl. No.: 09/597,225

(22) Filed: Jun. 20, 2000

(30) Foreign Application Priority Data

Jun. 21, 1999 (JP) ............................................ 11-174756

(51) Int. Cl.⁷ .......................... A01N 43/16; A61K 31/35
(52) U.S. Cl. ........................................ 514/460; 514/844
(58) Field of Search .................................. 514/460, 844

(56) References Cited

FOREIGN PATENT DOCUMENTS

| JP | 62-169720 | | 7/1987 |
|----|-----------|---|--------|
| JP | 08056612 | * | 3/1996 |
| JP | 2639386 | * | 8/1997 |

* cited by examiner

*Primary Examiner*—Alton Pryor
(74) *Attorney, Agent, or Firm*—McGinn & Gibb, PLLC

(57) ABSTRACT

The present invention provides deodorants that are characterized by palatinose-derived thermal decomposition as effective ingredients obtained by thermal decomposing the palatinose to 120–240 ° C. and also characterized by 6-(α-D-glucopyranosyloxy)-1,3,4-trihydroxyhexa-5-en-2-on, 5-[(αD-glucopyranosyloxy)methyl]-2-furancarboxaldehyde and the mixture of above as effective ingredients, so that deodorants posses strong deodorizing effect against various ingredients of odor at wide range of pH, and the addition of large amount to foods, beverages and oral compositions does not influence on their original flavor and good flavor.

15 Claims, No Drawings

DEODORANTS, FOODS AND BEVERAGES, AND ORAL COMPOSITIONS AS WELL AS TOILETRY PRODUCTS

BACKGROUND OF THE INVENTION

1. Field of the Invention

This invention relates to a deodorant including a main component of a decomposition obtained by thermally decomposing a palatinose, foods and beverages including the deodorant, and an oral composition including the deodorant as well as a toiletry product including the deodorant.

2. Description of the Related Art

Recently, people's intention to sanitation has been on the increase with an improvement of environmental sanitation, and people's interest in the odors regarding to the living environment and the human body has also been on the increase. The ode breath odor and the body odor provide particular influences to the human relationships. In this circumstances, various deodorant-related merchandises have been proposed to improve them, and they have now been about to be widely accepted by consumers. The breath odors are due to odors derived from foods consumed, odors from bacteria in the mouth and odors from stomach. Moreover, the odor ingredients nay comprise sulfide, nitride and organic acids. Particularly, even a slight amount of sulfide affects on the breath odor. Typical ones of the known sulfide are hydrogen sulfide, methyl mercaptan and dimethyl sulfide. It has been known that particularly after the consumption of garlic and onion, mounts of sulfide of allyl mercaptan, diallyl sulfide and diallyl sulfide are remarkably increased.

Currently, catechin as a green tea extract has widely been used as a typical deodorant. It has been known that catechin reacts with sulfides like methyl marcapton which is the major cause of the breath odor (Biosci. Biotech. Biochem., 59(7) 1232–1236, 1995). However, catechin has a strong bitter and acerbic taste and deteriorates an original flavor of food, it is necessary to limit the usable amount of catechin. Moreover, catechin shows its deodorizing effect under the neutral or alkaline condition. The reactivity of catechin decreases under the acidic condition, thereby reducing the deodorizing effect thereof. For this reason, even though sour deodorant foods are designed by adding catechin, the deodorant substance almost unreacts with the odor substance, and the deodorizing effect is insufficient.

Also, in Japanese laid-open publication 62–169720, it is also disclosed that caramels and maltols (3-hydroxy-2-methyl-γ-pyrone) obtained from heating sucrose or glucose show deodorizing effect against garlic and onion odors. If, however, the odor composition was analyzed by a gas chromatography, then no change in odor composition was observed. Furthermore, if the same analysis to sulfides such as methyl marcaptan and allyl marcaptan which comprise garlic and onion odor ingredients was carried out, then no change in the composition was observed. From those results, the deodorizing effect of caramels and maltols against the garlic and onion odors is the masking effect utilized by their strong scents and does not directly act on the ingredients of the odor.

On the other hand, a palatinose condensate prepared from heating palatinose is described in Japanese Patent No.2639386 entitled "palatinose and method of preparing the same and method of the use". The palatinose condensates as described are oligo-saccharides in various combinations of glucose with fructose as condensed. In those oligo-saccharides, palatinose condensates (syrup) prepared by using the process described in the patent publication are analyzed in the deodorizing activity against the sulfide (methyl marcapton), no considerable deodorizing activity is shown. Also palatinose condensate (palatinose oligosaccharide) purified by $NH_2$ silica gel column has a further reduced deodorizing activity. Therefore, palatinose condensates prepared from palatinose by the process described in the above patent publication have no deodorizing activity.

SUMMARY OF THE INVENTION

Accordingly, it is an object of the present invention to solve the above problem and to provide a deodorant which provides a strong deodorizing effect against various ingredients of odor in a wide pH range, provided that addition of a large amount thereof to foods, beverages and oral compositions provide no influence on their original and good flavors.

Furthermore, the present invention is to provide foods, beverages, oral compositions and toiletry products which provide strong deodorizing effects against various ingredients of odor in a wide pH range without deteriorating the flavor due to bitter and acerbic taste of the conventional deodorants.

This invention is to solve the problems mentioned above, and to provide deodorants that are characterized by palatinose-derived thermal decomposition included as effective ingredients obtained by thermally decomposing the palatinose. The term "palatinose-derived thermal decomposition" is defined to be a substance or product which is obtained by thermally decomposing palatinose. A palatinose-derived thermal decomposition obtained by thermally decomposing the palatinose in the range of 120–240° C. (particularly 140–200° C.) is desirable.

Also, is invention provides a deodorant characterized by 6-(α-D-glucopyranosyloxy)-1,3,4-trihydroxyhexa-5-en-2-on included therein as effective ingredient represented by the following structural formula (I):

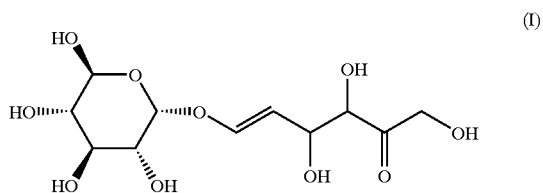

or a deodorant characterized by 5-[(α-D-glucopyranosyloxy)methyl]-2-furancarboxaldehyde included therein as effective ingredient represented by the following structural formula (II):

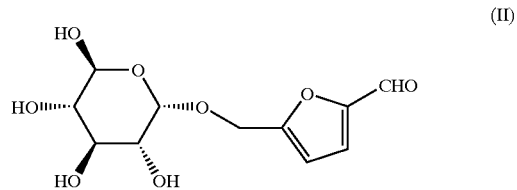

or deodorant characterized by mixture of above as effective ingredients.

Furthermore, the present invention provides foods, beverages, oral compositions and toiletry products inclusive of the above novel deodorants.

DISCLOSURE OF THE INVENTION

The resent inventors have researched on various materials to discover the effective deodorant in the head-space method using a gas chromatography. As a result, it was confirmed that a palatinose-derived thermal decomposition obtained by thermally decomposing the palatinose has a strong deodorizing effect against methyl mercaptan which is the typical composition of odor. Unheated palatinose does not provide such the effect. The effect is obtained upon heating process. Also, if other sugars were heated and prepared, then the palatinose-derived thermal decomposition of the present invention has shown higher deodorizing effects than the other sugars heated under the same conditions. Moreover, the palatinose-derived thermal decomposition of the present invention has also show a deodorizing effect against ammonia which is one of nitrides as odor.

Thus, the palatinose-derived thermal decomposition obtained by thermally decomposing the palatinose in accordance with the present invention serves as a deodorant which provides deodorizing effects against various ingredients of odor such as sulfides, nitrides, and a fatty acid.

In order to obtain the palatinose-derived thermal decomposition, it is necessary to heat the palatinose. For example, powders of palatinose and water are put in a stainless cup to prepare a solution. This solution is stirred and heated in a cooker to a final temperature in the range of 120–240° C. This final temperature should desirably be set in the range of 140–200° C. If the solution is heat at a high temperature, then the caramel odor becomes strong and flavor worsens. If, however, a priority is given to the deodorizing effect, the final temperature of the palatinose solution is set higher, for example, the palatinose solution is heated up to approximately 200° C. to prepare the palatinose-derived thermal decomposition with the desired strong deodorizing effect.

As to the other conditions than the temperature, the palatinose-derived thermal decomposition may be prepared under normal, high or low pressure. For the heating method, it is possible to use a boiler, a continuous heat-exchange method, and an extruder.

Also, it has commonly been known that acids and alkalis act as catalysts to caramelization of sugar. It is possible to use acids and alkalis as catalysts to prepare the palatinose-derived thermal decomposition of the present invention. A small amount of the deodorant active substance is formed upon use of alkali. In contrast, the formation of the deodorant active substance is promoted upon use of any acid. It is available to select any one or more from a hydrochloric acid, a sulfuric acid, an acetic acid, a citric acid, a lactic acid, an ascorbic acid, a gluconic acid, a malic acid, a tartaric acid and a fumaric acid.

A mixing ratio of water and palatinose may optionally be set. If the concentration of palatinose is low, then it takes a long time necessary for reaching the final temperature, and it is undesirable in view of the heat efficiency. It is also possible to heat the powdered palatinose alone at a temperature which is higher than its melting point of 122–124° C., and for example, in the range of 125–240° C., and preferably in the range of 140–200° C.

The time of heating the palatinose solution and palatinose powders may optionally be selected to obtain the heat-decomposed palatinose. If the temperature is relatively low, then a long time heating is required. At a high temperature, the palatinose-derived thermal decomposition can be prepared in a short time. It is preferable that the temperature is so set that the palatinose-derived thermal decomposition is obtained in the range of time from 5 minutes to 4 hours. Heating time depends on the amount prepared. For example, if the amount of prepared palatinose is large, then it takes a long time for heating the large amount of the palatinose to obtain a large amount of the palatinose-derived thermal decomposition. If the amount of prepared palatinose is small, then it takes a short time for heating the mall amount of the palatinose to obtain a small amount of the palatinose-derived thermal decomposition. For example, the palatinose-derived thermal decomposition showing the deodorizing activity may efficiently be prepared by heating 5g of palatinose powders at 160° C. for 2 hours. However, a long time heating at a high temperature causes decomposition and polymerization of active deodorant substances, and the deodorizing activity decreases. It is also possible for use to purify and concentrate the active substances in the palatinose-derived thermal decomposition by purification methods such as column chromatography and solvent extraction.

The present inventors have further researched on ingredients having the deodorizing activity contained in the palatinose-derived thermal decomposition and discovered that compounds, 6-(α-D-glucopyranosyloxy)-1,3,4-trihydroxyhexa-5-en-2-on (hereinafter referred to as GDH) and 5-[(α-D-glucopyranosyloxy)methyl]-2-furancarboxaldehyde (hereinafter referred to as GMF) have strong deodorizing effects although GMF is lower in deodorizing effect than GDH.

If the palatinose-derived thermal decomposition is analyzed by a high performance liquid chromatography (HPLC) under the following conditions, then GDH and GMF are eluded at 3.41 and 20.63 minutes, respectively.

| Conditions of High Performance Liquid Chromatography | |
|---|---|
| Column | Senshu Pak. PEGASIL ODS (4.6 φ × 250 mm) |
| Column Temperature | 40° C. |
| Effluent | Water |
| Rate of Elution | 0.5 ml/min. |
| Detector | UV detector (280 nm) |

Structural formula, chemical formula and characteristic spectral data of the compound GDH are indicated below.

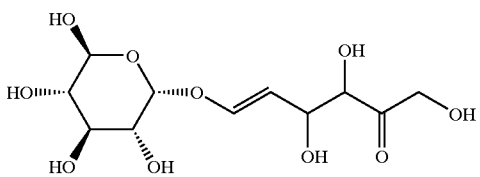

(I)

| | |
|---|---|
| Chemical formula | $C_{12}H_{18}O_9$ |
| $^1$H-NMR Spectrum (δ) | 7.11(1H, dd, J=3.5, 16.0Hz), 6.60 (1H, d, J=16.0), 5.48(2H, s), 5.28 (1H, d, J=3.5) |
| $^{13}$C-NMR Spectrum (δ) | 200.1, 152.1, 133.9 |
| MS Spectrum (CI-MS) | 324 m/z (M+1) |

Structural formula, chemical formula and characteristic spectral data of the compound GDH are indicated below.

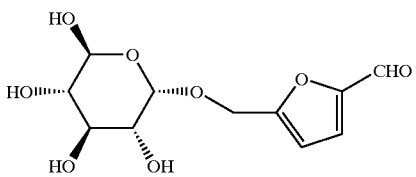

| | (II) |
|---|---|
| Chemical formula | $C_{12}H_{16}O_8$ |
| $^1$H-NMR Spectrum ($\delta$) | 9.49(1H, s), 7.32(1H, d, J=3.6Hz), 6.65(1H, d, J=3.6Hz) |
| $^{13}$C-NMR Spectrum ($\delta$) | 179.6, 159.5, 154.2, 124.4, 113.0 |
| MS Spectrum (CI-MS) | 289 m/z (M+1) |

GDH and GMF in the present invention can be prepared by thermally decomposing the palatinose followed by the use of the liquid chromatography as mentioned above. They may also be prepared by other methods without heating palatinose. It is possible to use each of GDH and GMF solely or in combination.

The deodorant in accordance with the present invention, namely, the palatinose-derived thermal decomposition, one obtained by purifying and concentrating the palatinose-derived thermal decomposition, and the compound GDH and the compound GMF may be used directly. Notwithstanding, generally, they are dissolved or dispersed in a proper liquid support. Alternatively, they are mixed with proper powders or with a solid support or are adsorbed therewith or impregnated thereto. If necessary, they are further added with emulsifiers, dispersing agents, suspending agents, spreaders, penetrants, wetting agents, and stabilizers for use as the products of emulsions, oil solutions, hydration agent, powder materials, tablets, sprays and solid agents.

As foods and beverages containing the above mentioned deodorant, in accordance with the present invention, a wide range of food and beverage such as chewing gums, candies, tablets, gummy-jellies and drinks are available. As oral compositions, mouthwash, toothpaste and troches are available. As for toiletry products, air fresheners, deodorants and deodorizing wet tissues for toilet, indoor use, car-use and garbage-use are available.

Further, since the deodorant in accordance with the present invention is effective under acidic conditions, the deodorant has a superior deodorizing effect upon use for sour foods and drinks and oral compositions.

Whereas modifications of the present invention will be apparent to a person having ordinary skill in the art, to which the invention pertains, it is to be understood that examples as shown and described by way of illustration are by no means intended to be considered in a limiting sense. Accordingly, it is to be intended to cover by claims all modifications which fall within the spirit and scope of the present invention.

EXAMPLE 1

100 g of a 50% palatinose solution was added into a stainless beaker to boil the same up to a temperature of 200° C. by use of a gas cooker, thereby obtaining 45 g of a palatinose-derived thermal decomposition.

COMPARATIVE EXAMPLE 1

100 g of sucrose solution was heated in the same manner as Example 1 to obtain 47 g of a heated sucrose.

EXAMPLE 2

5 g of palatinose powders was heated in an oven for 2 hours at 160° C., to obtain 4.6 g of a palatinose-derived thermal decomposition.

COMPARATIVE EXAMPLE 2:

5 g of sucrose was heated in the same manner as Example 2 to obtain 4.8 g of the heated sucrose.

EXAMPLE 3

A citric acid was added at 0.01% to 100 g of a 50% palatinose solution for the same process as Example 1 to obtain 46 g of an acid-added palatinose-derived thermal decomposition.

EXAMPLE 4

5 g of palatinose powders was heated under a low pressure in a vacuum oven for 2 hours at 160° C. to obtain 4.4 g of a low-pressure treated palatinose-derived thermal decomposition.

EXAMPLE 5

Using a silica gel column, 50 g of the palatinose-derived thermal decomposition of Example 1 was eluded in 3000 ml of a solvent having a chloroform to methanol ratio of 4:1, and further eluded with a solvent of a chloroform-to-methanol ratio of 1:1. The later elute was concentrated to obtain 17 g of a crude purified palatinose-derived thermal decomposition.

EXAMPLE 6

The crude purified palatinose-derived thermal decomposition of Example 5 as solution was fractionated, and a compound eluded at 6.6 minutes by HPLC under a fractional condition described below was dried to obtain GDH.

| Condition of High Performance Liquid Chromatography | |
|---|---|
| Column | Senshu Pak. ODS 5251-SH (20 φ × 250 mm) |
| Column Temperature | Room Temperature |
| Effluent | Water |
| Rate of Elution | 10.0 ml/min |
| Detector | UV detector (210 nm) |

EXAMPLE 7

The crude purified palatinose-derived thermal decomposition of Example 5 as a solution was fractionated, and a compound eluded at 9.2 minutes by HPLC at the fractional condition described below was dried to obtain GMF.

| Condition of High Performance Liquid Chromatography | |
|---|---|
| Column | Senshu Pak. ODS 5251-SH (20 φ × 250 mm) |
| Column Temperature | Room Temperature |
| Effluent | 20% Methanol |
| Rate of Elution | 10.0 ml/min |
| Detector | UV detector (280 nm) |

EXAMPLE 8

Hard Candy

A stamping molding was carried out at the following blending ratios in the normal manner to prepare hard candies, each of which is of 3 g. The heated palatinose prepared in Example 1 was used. As Comparative Example 3, the hard candies free of the palatinose-derived thermal decomposition was prepared.

TABLE 1

|  | Example 8 | Comparative Example 3 |
|---|---|---|
| Sucrose | 50.0 | 50.0 |
| Starch Syrup | 47.8 | 49.8 |
| Palatinose-derived thermal decomposition | 2.0 | — |
| Fragrance | 0.2 | 0.2 |
| Total | 100 | 100 |

% by weight

EXAMPLE 9

Sour Type Hard Candy

A Stamping molding was carried out at the following blending ratios in the normal manner to prepare hard candies, each of which is of 3 g. The heated-decomposed palatinose prepared in Example 1 was used. As Comparative Example 4, a hard candy free of the palatinose-derived thermal decomposition was prepared.

TABLE 2

|  | Example 9 | Comparative Example 4 |
|---|---|---|
| Sucrose | 50.0 | 50.0 |
| Starch Syrup | 46.3 | 48.3 |
| Palatinose-derived thermal decomposition | 2.0 | — |
| Fragrance | 0.2 | 0.2 |
| Citric acid | 1.5 | 1.5 |
| Total | 100 | 100 |

% by Weight

EXAMPLE 10

Tablet

Tablets, each of which is of 1.5 g, were prepared at the following blending ratios in the normal manner. The heated-decomposed palatinose prepared in Example 2 was used. As Comparative Example 5, tablets without using palatinose-derived thermal decomposition were prepared.

TABLE 3

|  | Example 10 | Comparative Example 5 |
|---|---|---|
| Sucrose | 82.3 | 84.3 |
| Glucose | 10.0 | 10.0 |
| Sucrose fatty acid ester | 1.0 | 1.0 |
| Palatinose-derived thermal decomposition | 2.0 | — |
| Water | 4.2 | 4.2 |
| Fragrance | 0.5 | 0.5 |
| Total | 100 | 100 |

% by Weight

EXAMPLES 11 and 12

Chewing Gum

A mixing process was carried out by a needle mixer at the following blending ratios in the normal manner to prepare sheet-shaped chewing gums, each of which is of 3.0 g. The heated-decomposed palatinose prepared in Example 3 was used. As Comparative Examples 6 and 7, chewing gums added with palatinose in spite of the palatinose-derived thermal decomposition was prepared.

TABLE 4

|  | Example 11 | Example 12 | Comparative Example 6 | Comparative Example 7 |
|---|---|---|---|---|
| Gum base | 13 | 13 | 13 | 13 |
| Sucrose | 55 | 55 | 55 | 55 |
| Glucose | 10 | 10 | 10 | 10 |
| Starch syrup | 20 | 20 | 20 | 20 |
| Mint fragrance | 1.0 | — | 1.0 | — |
| Citric acid | — | 0.5 | — | 0.5 |
| Lemon fragrance | — | 0.5 | — | 0.5 |
| Palatinose-derived thermal decomposition | 1.0 | 1.0 | — | — |
| Palatinose | — | — | 1.0 | 1.0 |
| Total | 100 | 100 | 100 | 100 |

% by Weight

EXAMPLE 13

Drink

A drink was prepared at the following blending ratios in the normal manner. The heated-decomposed palatinose prepared in Example 1 was used. As Comparative Example 8, the drink free of palatinose-derived thermal decomposition was prepared.

TABLE 5

|  | Example 13 | Comparative Example 8 |
|---|---|---|
| Fructose glucose solution | 5.0 | 5.0 |
| Honey | 5.0 | 5.0 |
| Palatinose-derived thermal decomposition | 2.0 | — |
| Fragrance | 0.1 | 0.1 |
| Synthetic preservative | 0.01 | 0.01 |
| Purified water | 87.89 | 89.89 |
| Total | 100.0 | 100.0 |

% by Weight

EXAMPLE 14

Mouth Wash

A mouth wash was prepared at the following blending ratios in the normal manner. The heated-decomposed palatinose prepared in Example 3 was used. As Comparative Example 9, a mouth wash free of palatinose-derived thermal decomposition was prepared.

TABLE 6

|  | Example 14 | Comparative Example 9 |
|---|---|---|
| Ethanol | 20.0 | 20.0 |
| Sodium lauric acid | 1.0 | 1.0 |
| Palatinose-derived thermal decomposition | 2.0 | — |

TABLE 6-continued

|  | Example 14 | Comparative Example 9 |
|---|---|---|
| Fragrance | 1.5 | 1.5 |
| Glycerol | 10.0 | 10.0 |
| Sodium dihydrogenphosphate | 0.5 | 0.5 |
| D-sorbitol | 5.0 | 5.0 |
| Water | 60.0 | 62.0 |
| Total | 100.0 | 100.0 |

% by Weight

EXAMPLE 15

Hard Candy

A stamping molding was carried out at the following blending ratios in the normal manner to prepare hard candies, each of which is of 3 g. GDH isolated and purified by HPLC was used.

TABLE 7

|  | Example 15 |
|---|---|
| Sucrose | 50.0 |
| Starch Syrup | 49.3 |
| GDH | 0.5 |
| Fragrance | 0.2 |
| Total | 100 |

% by Weight

TEST 1

Deodorizing Effect Test

The palatinose-derived thermal decomposition and the heat-decomposed sucrose were respectively dissolved into 0.2 M phosphoric acid buffer (pH 7.5) to have 7.5 mg/ml concentration respectively. After 1.0 ml of the sample solution and 0.5 ml of 25 ppm sodium methylmercaptan was added in a vial to shake the same for 30 minutes at 37° C., and then 200 µl of a vapor phase component in the vial was gathered. An amount of formed methylmercaptan was measured by the gas chromatography to compare the same with a sample-free system, thereby to find a reduction ratio of methylmercaptan as a deodorizing coefficient. As comparison, non-heated palatinose, sucrose and palatinose oligosaccharide syrup were subjected to the deodorant tests respectively in the same manner.

The gas chromatography uses "GC-9A" commercially available from Shimazu Manufacturing Co., Ltd. The measuring conditions were described below.

| Column | 20% DOP (dioctylphthalate), Chromosorb W (AWDMCS) 5.0 m × 3.0 mm I.D |
|---|---|
| Column Temperature | 90° C. |
| Injection Temperature | 150° C. |
| Detector | FPD |
| Detected Temperature | 200° C. |
| Rate of Flow | 60 ml/min Carrier gas (N2 gas) |

The result is shown on Table 8.

TABLE 8

|  | Deodorant coefficient (%) |
|---|---|
| Example 1 | 58.7 |
| Comparative Example 1 | 3.5 |
| Example 2 | 41.4 |
| Comparative Example 2 | 2.4 |
| Example 3 | 60.8 |
| Example 4 | 59.2 |
| Example 5 | 98.9 |
| Palatinose | 0.0 |
| Sucrose | 0.0 |
| Palatinose oligosaccharide syrup | 3.9 |
| Palatinose oligosaccharide column purified product *) | 0.5 |

*)Oligosaccharide alone was purified from the palatinose oligosaccharide by NH2 silica gel column.

It was confirmed that the palatinose-derived thermal decomposition obtained by thermally decomposing the palatinose shows the deodorizing activity specifically.

TEST 2

Deodorizing Effect Test at pH 4.0

Each of the palatinose-derived thermal decomposition of Example 1 and the crude catechin of the green tea (catechin content 80%) was dissolved in to 0.2 M phosphoric acid buffer (pH 4.0) to have 5 mg/ml concentration respectively. After 1.0 ml of the sample solution and 0.5 ml of 12.5 ppm methylmercaptan sodium were added in the vial to shake the same for 3 hours at 37° C., and then 200 µl of the vapor phase component in the vial was gathered. An amount of obtained methylmercaptan was measured by the gas chromatography and compared to the sample free system to find a reduction ratio of methylmercaptan as a deodorizing rate. The result is shown on Table 9.

TABLE 9

|  | Rate of deodorizing (%) |
|---|---|
| Example 1 | 15.2 |
| Crude catechin of the green tea | 7.7 |

It was confirmed that the palatinose-derived thermal decomposition of the Example 1 obtained by boiling 50% palatinose solution shows the high deodorizing effect significantly as compared with the crude catechin of the green tea under acidic conditions at pH 4.0.

TEST 3

Deodorizing Effect Test Against Ammonia

Each of 50 mg of the palatinose-derived thermal decomposition of Example 1 and sodium copper chlorophyllin was dissolved into 1.96 ml of water in 100 ml of the vial respectively. Then, 40 µl of an ammonia solution (0.28%) was added and shaken for 5 minutes at 37° C. and 100 ml of the vapor phase component in the vial was measured under a vacuum pressure by use of a Kitagawa detecting tube (ammonia No.3). The deodorizing rate of each sample was calculated from the concentration of ammonia in case of addition of no sample. The result is shown on Table 10.

TABLE 10

| | Rate of deodorizing (%) |
|---|---|
| Example 1 | 42.0 |
| Sodium copper chlorophyllin | 9.2 |

It was confirmed that the heated palatinose of the Example 1 shows the high deodorizing effect significantly against ammonia as one nitrogen compound as compared with sodium copper chlorophyllin.

TEST 4

Deodorizing Effect Test of GDH

GDH compound in the present invention was dissolved into 0.2 M phosphoric acid buffer (pH 7.5) to have 0.5 mg/ml concentration. After 1.0 ml of the sample solution and 0.5 ml of 25 ppm sodium methylmercaptan solution we added in the vial to shake the same for 30 minutes at 37° C., and then 200 μl of the vapor phase component in the vial was gathered. An amount of the obtained methylmercaptan was measured by the gas chromatography and compared to the sample-free system to find the reduction rate of methylmercaptan as the deodorizing rate. The deodorizing activity was 36.3%.

TEST 5

Deodorizing Effect Test of GMF

GMF of compounds in the present invention was dissolved into 0.2 M phosphoric acid buffer (pH 7.5) to have 5.0 mg/ml concentration. After 1.0 ml of the sample solution and 0.5 ml of 25 ppm methylmercaptan sodium solution were added in the vial to shake the same for 30 minutes at 37° C., and then 200 μl of the vapor phase component in the vial was gathered. An amount obtained methylmercaptan was measured by the gas chromatography and compared to the sample free system to find the reduction rate of methylmercaptan as the deodorizing rate. The deodorizing activity was at 23.1%.

TEST 6

Deodorizing Effect Test of Candy

Candies of Examples 8, 9 and Comparative Examples 3, 4 were dissolved into 0.2 M phosphoric acid buffer (pH 7.5) to have 250 mg/ml concentration. After 1.0 ml of the sample solution and 0.5 ml of 25 ppm sodium methylmercaptan solution were added in the vial to shake the same for 30 minutes at 37 ° C., and then 200 μl of the vapor phase component in the vial was gathered. An amount of the obtained methylmercaptan was measure by the gas chromatography and compared to the sample free to find a reduction rate of methylmercaptan as the deodorizing rate. The result is shown on Table 11.

TABLE 11

| | Rate of deodorizing (%) |
|---|---|
| Example 8 | 48.6 |
| Comparative Example 3 | 7.6 |

TABLE 11-continued

| | Rate of deodorizing (%) |
|---|---|
| Example 9 | 44.3 |
| Comparative Example 4 | 6.3 |

It was confirmed that the candy added with the palatinose-derived thermal decomposition shows the high deodorizing effect against methylmercaptan. It was also confirmed that the palatinose candy of Example 9 as the deodorizing effect even the candy is of sour type.

TEST 7

Deodorizing Effect Test Against Garlic Odors of Candy by Organoleptics

The deodorizing effect of the candy of Example 8 was investigated. Five of commercially available garlic-containing Chaotzues were eaten. Immediately thereafter, 3 g of the candy was put into the mouth for 5 minutes, so that 3000 ml of exhalation was gathered in an odorless bag. In the same manner, after the Chaotzues were eaten, 3 g of the candy free of palatinose-derived thermal decomposition in Comparative Example 3 was put in the mouth for 5 minutes, then the exhalation was gathered in the odorless bag. The deodorizing effect against garlic odors was estimated functionality by the following criterions.

Criterions 5: intensive odor 4: strong odor 3: odor easily sensible 2: odor presumable of what kind of the smell 1: odor almost insensible 0: odorless The results are shows on Table 12.

TABLE 12

| Panelist | a | b | c | d | e | f | average |
|---|---|---|---|---|---|---|---|
| Example 8 | 0 | 2 | 1 | 2 | 1 | 1 | 1.2 |
| Comparative Example 3 | 3 | 3 | 4 | 4 | 3 | 4 | 3.5 |

As this result the candy with the palatinose-derived thermal decomposition showed the high deodorizing effect against the breath odor immediately after having the garlic.

TEST 8

The Deodorizing Effect Test Against Garlic Odors of Tablet by Organoleptics

The deodorizing effect of the tablet of Example 10 was investigated. Five of commercially available garlic-containing Chaotzues were eaten. Immediately thereafter, 3 g of the tablet of Example 10 was eaten (2 tablets, each of 1.5 g), so that 3000 ml of exhalation was gathered in an odorless bag. In the same manner, after five of the Chaotzues were eaten, 3 g of the tablet free of the heated palatinose of Comparative Example 5 was eaten, and then the exhalation was gathered in the odorless bag. The deodorizing effect was estimated functionality on the basis of the criterions of Test 5. The results are shown on Table 13.

TABLE 13

| | Panelist | | | | | | |
|---|---|---|---|---|---|---|---|
| | a | b | c | d | e | f | average |
| Example 10 | 1 | 2 | 1 | 2 | 2 | 1 | 1.5 |
| Comparative Example 5 | 4 | 4 | 4 | 3 | 5 | 4 | 4.0 |

It was confirmed that the tablet with the heated palatinose shows the high deodorizing effect against the breath odor immediately after eating the garlic.

TEST 9

Deodorizing Effect Test Against Garlic Odors of Chewing Gum by Organoleptics

The deodorizing effect of the chewing gum of Examples 11, 12 were investigated. Five of commercially available garlic-containing Chaotzues were eaten. Immediately after one sheet of the chewing gums of 3 g in Examples 11 and 12 was chewed for 5 minutes, then 3000 ml of exhalation was gathered in the odorless bag. In the same manner, after five of the Chaotzues were eaten, then the chewing gums of Comparative Examples 6, 7 free of the heated palatinose were chewed, so that the exhalation was gathered in the odorless bag. The deodorizing effect was estimated functionality on the basis of the criterions of Test 5. The results are shown on Table 14.

TABLE 14

| | Panelist | | | | | | |
|---|---|---|---|---|---|---|---|
| | a | b | c | d | e | f | Average |
| Example 11 | 1 | 2 | 1 | 0 | 1 | 1 | 1.0 |
| Example 12 | 1 | 1 | 1 | 0 | 0 | 1 | 0.7 |
| Comparative Example 6 | 3 | 3 | 2 | 2 | 4 | 3 | 2.8 |
| Comparative Example 7 | 4 | 2 | 2 | 2 | 2 | 3 | 2.3 |

It was confirmed that the chewing gums with the heated palatinose show the high deodorizing effect against the breath odor immediately after eating the garlic.

TEST 10

Deodorizing Effect Test Against Garlic Odors of Drink by Organoleptics

The deodorizing effect of the drink of Examples 13 was investigated. Five of commercially available garlic-containing Chaotzues were eaten. 300 ml of the beverages drunk, and then 3000 ml of exhalation was gathered in the odorless bag. In the same manner, the beverages of Comparative Examples 8 free of the heated palatinose were drunk while the Chaotzues were eaten, then the exhalation was gathered in the odorless bag. The deodorizing effect was estimated functionality on the basis of the criterions of Test 5. The results are shown on Table 15.

TABLE 15

| | Panelist | | | | | | |
|---|---|---|---|---|---|---|---|
| | a | b | c | d | e | f | Average |
| Example 13 | 2 | 1 | 3 | 2 | 2 | 2 | 2.0 |
| Comparative Example 8 | 5 | 4 | 5 | 4 | 3 | 4 | 4.2 |

It was confirmed that the beverages with the heated palatinose show the high deodorizing effect against the breath odor immediately after eating the garlic.

TEST 11

Deodorizing Effect Test Against Garlic Odors of Mouth Wash by Organoleptics

The deodorizing effect of the mouth wash of Examples 14 was investigated. Five of commercially available garlic-containing Chaotzues were eaten. Gargle was made three times by use of 50 ml of the mouth wash of Example 14, and then 3000 ml of exhalation was gathered in the odorless bag. In the same manner, the exhalation after having been gargled by the mouth wash of Comparative Examples 9 free of the heated palatinose was gathered in the odorless bag. The deodorizing effect was estimated functionality on the basis of the criterions of Test 5. The results are shown on Table 16.

TABLE 16

| | Panelist | | | | | | |
|---|---|---|---|---|---|---|---|
| | a | b | c | d | e | f | Average |
| Example 14 | 1 | 2 | 0 | 1 | 1 | 2 | 1.2 |
| Comparative Example 9 | 3 | 5 | 4 | 3 | 4 | 3 | 3.7 |

It was confirmed that the mouth wash with the heated palatinose shows the high deodorizing effect against the breath odor immediately after eating the garlic

TEST 12

Deodorizing Effect Test of Candy Contained with GDH

The candy of Example 15 was dissolved into 0.2 M phosphoric acid buffer (pH 7.5) to have 250 mg/ml concentration. After 1.0 ml of the sample solution and 0.5 ml of 25 ppm methylmercaptan sodium solution were added in the vial to shake the same for 30 minutes at 37 ° C., then 200 $\mu$l of the vapor phase component in the vial was gathered. An amount of the obtained methylmercaptan was measured by the gas chromatography and compared to the sample free system to find the reduction rate of methylmercaptan as the deodorizing rate. The results are shown on Table 17.

TABLE 17

| | Rate of deodorizing (%) |
|---|---|
| Example 15 | 90.8 |

In accordance with the present invention, this palatinose-derived thermal decomposition obtained by thermally decomposing the palatinose, for example, 6-($\alpha$-D-glucopyranosyloxy)-1,3,4-trihydroxyhexa-5-en-2-on and 5-[($\alpha$-D-glucopyranosyloxy)methyl]-2- furancarboxaldehyde is superior in deodorizing effect and flavor. Therefore, this palatinose-derived thermal decomposition provides the strong deodorizing effect against various ingredients of odor in a wide pH range. If a large amount of the palatinose-derived thermal decomposition is used for foods, beverages and oral compositions, then almost no influence is given to their original and good flavor.

Also foods, beverages, and oral compositions of the present invention have the strong deodorizing effect against various ingredients of odor in a wide pH range without deterioration to the flavor due to bitter and acerbic taste possessed by the conventional deodorants. Especially, the foods, beverages, and oral compositions of the present invention are effective to the our foods and beverages.

Furthermore, toiletry products of the present invention have the strong deodorizing effect against both odors from sulfides and nitrides. Therefore, this invention is applicable to various kinds of odors widely.

What is claimed is:

1. A deodorant having an effective ingredient comprising at least any one selected from 6-(α-D-glucopyranosyloxy)-1,3,4-trihydroxyhexa-5-en-2-on given the following structural formula (I):

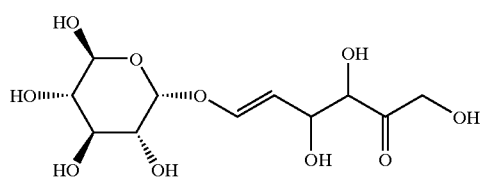

or 5-[(α-D-glucopyranosyloxy)methyl]-2-furancarboxaldehyde given by the following structural formula (11):

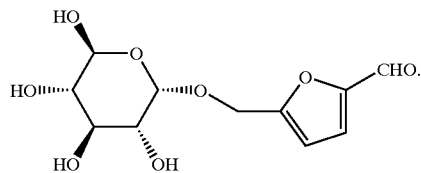

2. The deodorant according to claim 3, wherein said effective ingredient is obtained by thermally decomposing palatinose in the range of 120–240° C.

3. Foods and beverages comprising a deodorant as claimed in claim 2.

4. Foods and beverages comprising a deodorant as claimed in claim 1.

5. An oral composition comprising a deodorant as claimed in claim 2.

6. An oral composition comprising a deodorant as claimed in claim 1.

7. A toiletry product comprising a deodorant as claimed in claim 2.

8. A toiletry product comprising a deodorant as claimed in claim 1.

9. A deodorant comprising at least one of 6-( -D-glucopyranosyloxy)-1,3,4-trihydroxyhexa-5 en-2-on given by the following structural formula (1):

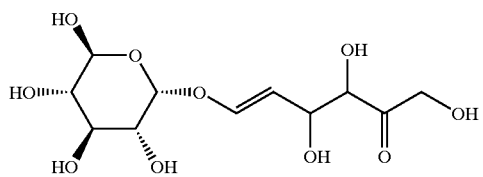

and 5-[ -D-glucopyranosyloxy)methyl]-2-furancarboxaldehyde given by the following structural formula (II):

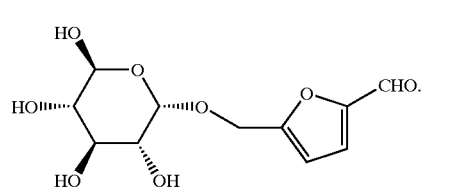

10. The deodorant according to claim 9, wherein said deodorant is in a concentration sufficient to deodorize sulfide and nitride odors.

11. The deodorant according to claim 9, wherein said deodorant comprises purified and concentrated palatinose-derived thermal decomposition.

12. The deodorant according to claim 9, wherein said deodorant further comprises at least one of an emulsifier, dispersing agent, suspending agent, spreader, penetrant, wetting agent and stabilizer.

13. The deodorant according to claim 9, wherein said deodorant has a deodorant coefficient of at lest about 41% based on a reduction ratio of methylmercaptan.

14. The deodorant according to claim 9, wherein at a pH of 4.0, said deodorant has a deodorant coefficient of at least about 15% based on a reduction ratio of methylmercaptan.

15. The deodorant according to claim 9, wherein said deodorant provides a deodorizing rate of at least about 42% based on a concentration of ammonia.

* * * * *